Dec. 3, 1963 J. M. GARABEDIAN Plant Pat. 2,324

PLUM TREE

Filed Oct. 29, 1962

WITNESS

Addison E. Avery

INVENTOR

John M. Garabedian

Webster & Webster

ATTYS.

United States Patent Office

Plant Pat. 2,324
Patented Dec. 3, 1963

2,324
PLUM TREE

John M. Garabedian, Fresno, Calif., assignor to Peach & Willow Farms, Inc., Fresno, Calif., a corporation of California Filed Oct. 29, 1962, Ser. No. 233,987
1 Claim. (Cl. Plt.—38)

This invention relates to a new and distinct variety of plum tree; such variety having been originated by me, in an experimental orchard located near Fresno, California, as a seedling from an unnamed and unpatented mutation of the Santa Rosa plum; the latter likewise being unpatented.

Upon such seedling reaching the point of bearing I recognized that it had certain distinctive characteristics—as will hereinafter appear—and thereafter I selected the variety for asexual reproduction.

Such asexual reproduction was accomplished by me, in the aforesaid experimental orchard, by budding on mature peach root stock. Such reproductions ran true to the parent in all respects.

While the present variety has general similarity to the Santa Rosa in tree and fruit, the following—in comparison—are the primary distinctive characteristics:

The tree of the present variety, although properly classed as vigorous and upright in growth, is of slightly less vigor and tends to spread a little more than the Santa Rosa.

The tips of the flower buds of the present variety, as the folded petals are first exposed, are pink, whereas the tips of the flower buds of the Santa Rosa are white.

The clingstone fruit of the present variety is in harvest approximately two weeks earlier than that of the Santa Rosa, and further—while similar in shape—has a brighter yellow ground color—as the fruit matures—beneath the substantially entire overspreading of red.

Figure 1:
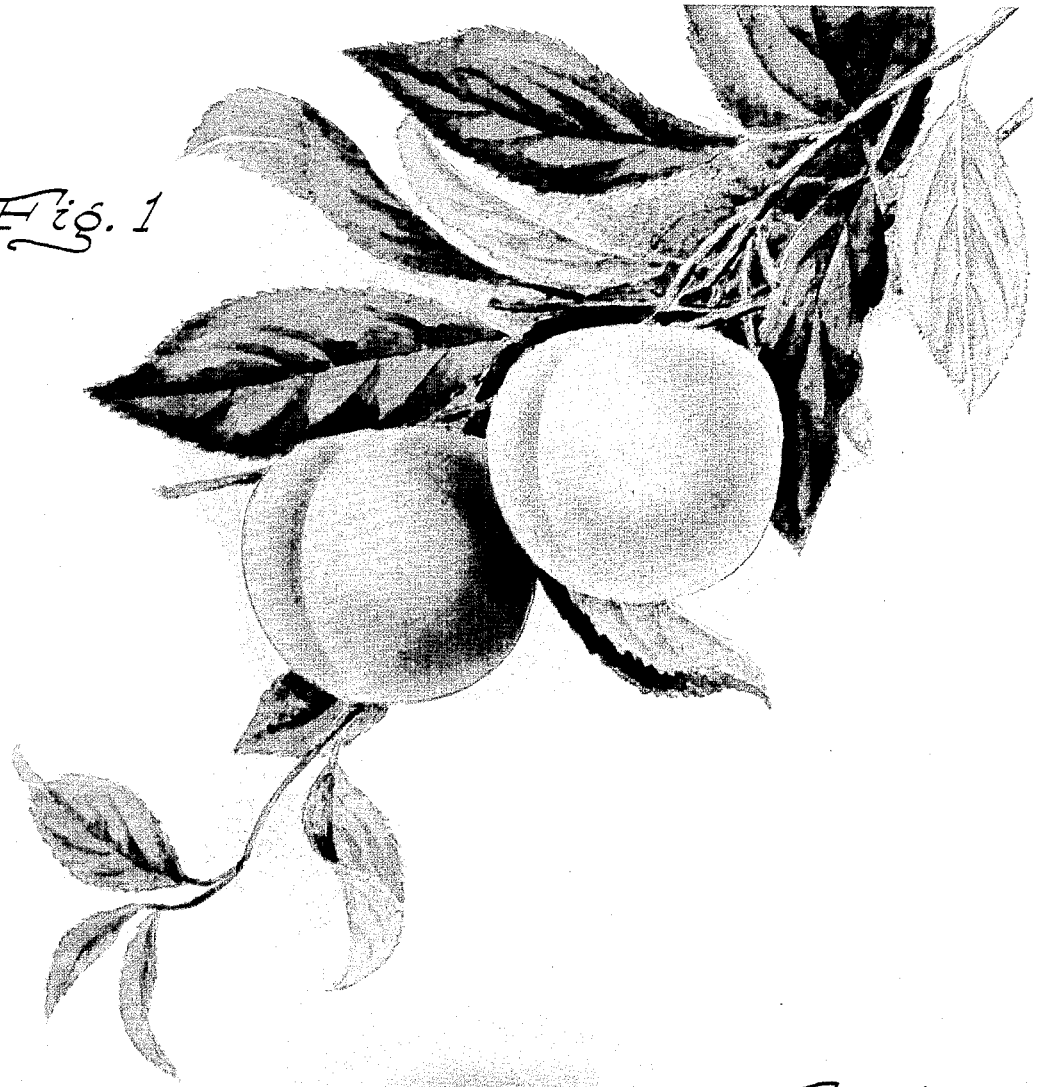
FIG. 1 is an elevation showing two of the fruit, together with twigs and leaves.
Figure 2:
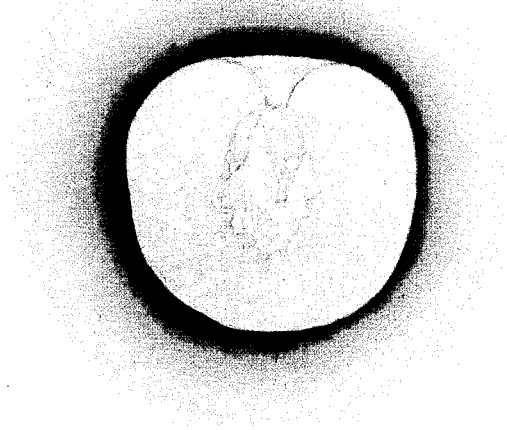
FIG. 2 is a sectional elevation of one of the fruit, with the stone remaining in place and partially showing.

Referring now more specifically to the pomological details of this new and distinct variety of plum tree, the following is an outline description thereof; all major color plate identifications being by reference to Maerz and Paul Dictionary of Color, except where common terms of color definition are employed.

Tree:
- *Size.*—Large.
- *Vigor.*—Vigorous.
- *Growth.*—Upright.
- *Density.*—Dense.
- *Form.*—Vase-shaped.
- *Hardiness.*—Hardy as Santa Rosa.
- *Production.*—Very productive.
- *Bearing.*—Regular bearer.

Trunk: Size—medium.

Branches:
- *Size.*—Medium.
- *Color.*—Young growth—green. Mature growth—brown.
- *Lenticels.*—Number—numerous. Size—medium.

Leaves:
- *Size.*—Medium. Average length—2½". Average width—1¼".
- *Form.*—Acuminate; acutely pointed.
- *Thickness.*—Thin; young leaves leathery.
- *Surface.*—Smooth; shiny.
- *Color.*—Top side—medium green (23–L–6) with slight yellow caste. Under side—lighter green (22–I–5).
- *Margin.*—Crenate.
- *Petiole.*—Medium length.
- *Glands.*—Average number—three. Irregular in position; small.
- *Stipules.*—Small; linear; light green; dehiscent.

Flower buds:
- *Hardiness.*—Hardy.
- *Size.*—Medium to small.
- *Length.*—Medium.
- *Form.*—Conic to pointed.
- *Surface.*—Glabrous.
- *Color.*—Pale to pink tip when bud starts to open.

Flowers:
- *Blooming period.*—Date of first bloom—March 1st. Date of full bloom—March 5th. Medium to late as compared with other varieties.
- *Size.*—Medium to small.
- *Color.*—White.

Fruit:
- *Maturity when described.*—Hard ripe—June 1st–June 5th.
- *Date of first picking.*—June 1st.
- *Date of last picking.*—June 5th.
- *Comparative harvest.*—Approximately two weeks earlier than the Santa Rosa.
- *Size.*—Uniform; medium. Average diameter axially—1 9/16" to 2". Average transversely in suture plane—1 9/16 to 2⅛".
- *Form.*—Uniform; symmetrical; globose.
- *Suture.*—Shallow; extends from base to slightly beyond pistil point.
- *Ventral surface.*—Round; lips equal.
- *Cavity.*—Flaring; rounded. Elongated in suture plane, with suture showing on one side. Average depth—¼" to ½". Average breadth—½" to ¾".
- *Base.*—Rounded to truncate.
- *Apex.*—Short; rounded.

Skin:
- *Thickness.*—Medium.
- *Texture.*—Medium.
- *Tenacity.*—Tenacious to flesh.
- *Tendency to crack.*—None in dry season.
- *Down.*—Wanting.
- *Color.*—Red (3–L–9 to 3–L–12) entirely overspreading a bright yellow ground color. Light greyish bloom.

Flesh:
- *Amygdalin.*—Scant.
- *Texture.*—Firm.
- *Fibers.*—Few; fine.
- *Ripens.*—Evenly.
- *Flavor.*—Slightly acid.
- *Aroma.*—Distinct.
- *Eating quality.*—Excellent.
- *Color.*—Yellow (11–L–4 to 12–K–4), shading darker to an orange red (3–I–11). Surface of pit cavity—slightly red, increasing with maturity.

Stone:
- *Type.*—Cling. Adheres to flesh over entire surface and along both dorsal and ventral edges. Short fibers.
- *Size.*—Medium. Average length—¾" to 1". Average breadth—½" to ⅝". Average thickness—5/16" to 7/16".
- *Form.*—Globose to oval.
- *Base.*—Irregular.
- *Hilum.*—Narrow; small.
- *Apex.*—Rounded; broad; slightly pointed.
- *Sides.*—Equal.

*Surface.*—Shallow irregular furrows near base and ventral edge.

*Pitting.*—Throughout, very shallow.

*Ridges.*—Interrupted; rounded toward base.

*Dorsal edge.*—Narrow, with shallow groove throughout.

*Tendency to split.*—Slight.

*Color.*—Light brown (10–H–7).

Use: Market.

Keeping quality: Good.

Shipping quality: Good to excellent.

The tree and its fruit herein described may vary in slight detail due to climatic and soil conditions under which the variety may be grown; the present description being of the variety as grown near Fresno, California.

The following is claimed:

A new and distinct variety of plum tree, as illustrated and described, having general similarity in tree and fruit to the Santa Rosa, but distinctively characterized—in comparison—by flower buds having pink tips instead of white, and clingstone fruit which is in harvest approximately two weeks earlier, such fruit having an entire exterior red color, the latter overspreading a yellow ground color brighter than that of said Santa Rosa.

No references cited.